United States Patent [19]

Fukui et al.

[11] Patent Number: 4,961,692
[45] Date of Patent: Oct. 9, 1990

[54] OSCILLATING VESSEL PUMP

[76] Inventors: Yasuhiro Fukui, 52-10-1--3, 5-chome, Higashiikebukro, Toshima-ku, Tokyo; Osamu Miyashita, 2-5, 2-chome, Takakura, Iruma-shi, Saitama-prf., both of Japan

[21] Appl. No.: 352,344

[22] Filed: May 16, 1989

Related U.S. Application Data

[62] Division of Ser. No. 185,029, Apr. 22, 1988, Pat. No. 4,869,650.

[30] Foreign Application Priority Data

Apr. 22, 1987 [JP] Japan .................................. 62-97436

[51] Int. Cl.$^5$ .............................................. F04B 7/00
[52] U.S. Cl. .................................. 417/241; 417/424.2
[58] Field of Search ................... 417/240, 241, 423.14, 417/424.2; 415/182.1, 206, 900

[56] References Cited

U.S. PATENT DOCUMENTS

| 2,674,404 | 4/1954 | Wieseman | 417/423.14 |
| 3,082,940 | 3/1963 | Frantz | 417/423.2 X |
| 3,617,153 | 11/1971 | Mowry . | |
| 3,746,465 | 7/1923 | Van Doorn et al. | 415/206 |
| 3,824,035 | 7/1974 | Laing | 417/423.14 X |
| 4,120,616 | 10/1978 | Dwyer et al. | 417/423.2 X |

FOREIGN PATENT DOCUMENTS

| 0486575 | 11/1929 | Fed. Rep. of Germany . | |
| 0987207 | 1/1983 | U.S.S.R. | 417/241 |
| 0987208 | 1/1983 | U.S.S.R. | 417/241 |
| 1002682 | 3/1983 | U.S.S.R. | 417/241 |
| 1092307 | 5/1984 | U.S.S.R. | 417/240 |

OTHER PUBLICATIONS

Vanderhorst, "The Outperformer", Feb. 1984.

Primary Examiner—Leonard E. Smith
Assistant Examiner—Eugene L. Szczecina, Jr.
Attorney, Agent, or Firm—Oblon, Spivak, McClelland, Maier & Neustadt

[57] ABSTRACT

The present invention provides a pump by vessel oscillation including a vessel having an inlet for liquid and an outlet opening in a specific tangential direction of an outer peripheral portion thereof. The vessel is oscillated in a specific direction to outflow the liquid through the outlet opening. Accordingly, the liquid in the interior of the vessel undergoes a simple centrifugal motion and when the pump is used for a blood circulation device such as an artificial heart or assisted circulation device, the blood is completely shut off from outside and isolated from entry of various germs, air, foreign matter, etc. The pump is simple is construction and excellent in reliability and durability.

2 Claims, 4 Drawing Sheets

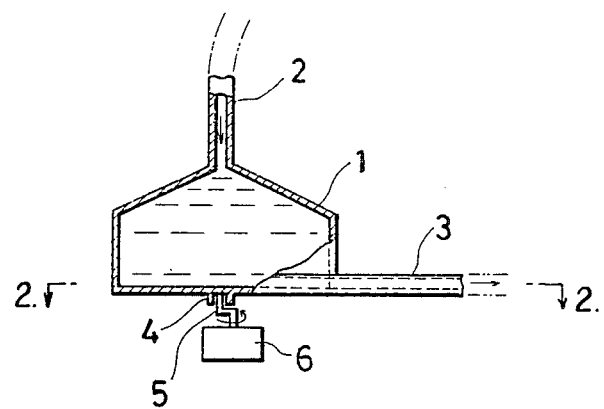
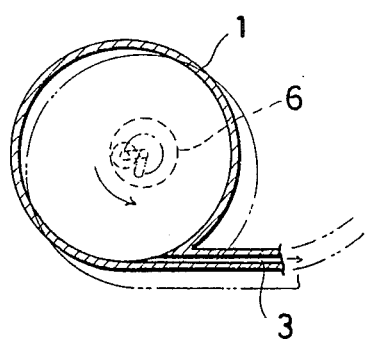
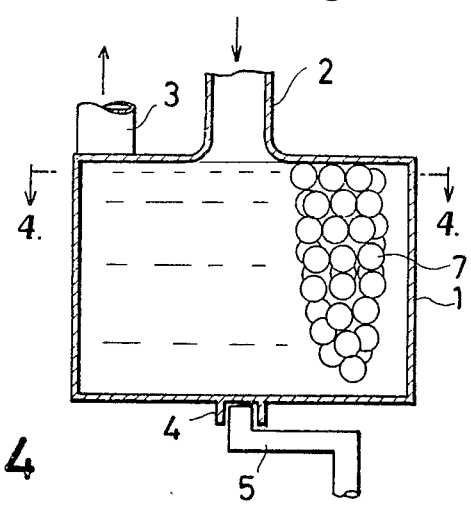
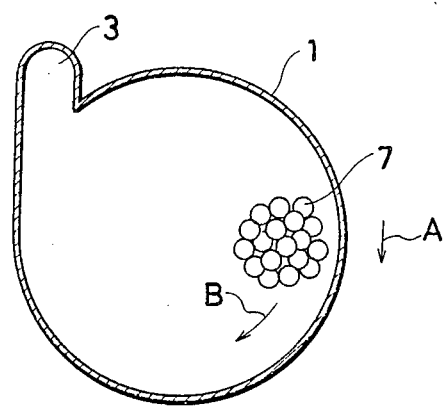

OSCILLATING VESSEL PUMP

This is a division of application Ser. No. 07/185,029, filed on Apr. 22, 1988, now U.S. Pat. No. 4,8969,650.

BACKGROUND OF THE INVENTION

1. Field of the Invention:

The present invention relates to a centrifugal pump for circulating a liquid, and more particularly to a pump operating by vessel oscillation, suitable for a blood circulation device such as an artificial heart or an assisted circulation device or the like.

2. Discussion of the Background:

In the past, pumps of this kind have been known which are designed, for example, as shown in FIGS. 11 and 12. More specifically, they comprise a vessel (a), an outlet opening (b) provided in a tangential direction of an outer periphery at the lower part of the vessel (a), and an inlet (c) in the central portion at the upper part of the vessel (a). A sealed rotary shaft (d) is provided in the central portion at the lower part of the vessel (a), the rotary shaft (d) being extended within the vessel (a). An umbrella-like rotor (e) is secured to the end of the shaft within the vessel, the rotor (e) and shaft (d) being rotated by a drive device (not shown) from the bottom of the shaft.

In the pump constructed as described above, the liquid flowing into the vessel (a) from the upper inlet (c) is rotated by the rotation of the rotor (e) and formed into a centrifugal flow which flows out of the outlet opening (b).

Accordingly, in the case where the above-described pump is used for the artificial heart or the like, the rotor rotates within the vessel and therefore various germs, air, foreign matter or the like are possibly mixed with the blood via the bearing, which might cause hemolysis (destruction of red blood cells) or thrombus (condensation of blood). In addition, since the bearing for rotating the rotor is provided on the vessel, the low durability of the bearing portion, particularly a seal of the bearing has disadvantages.

SUMMARY OF THE INVENTION

A first object of the present invention is to eliminate the need of a rotating article within the vessel and eliminate a bearing seal for a rotary shaft of said rotating article. Therefore, when the pump is used for the device for circulating blood such as an artificial heart or a device for assisted circulation, the blood is completely shut off from the outside to prevent the entry of various germs, air, foreign matter or the like. A second object of the invention is to simplify the construction to provide high reliability and durability.

For achieving these objects, the present invention is characterized in that a vessel having a liquid inlet and formed with an outlet opening in a specific tangential direction in the outer peripheral portion of the vessel can be oscillated in a specific direction around an axis. Due to the oscillation of the vessel itself, the fluid flowing into the vessel from the inlet undergoes a circular motion to produce a centrifugal flow. Since in the outer peripheral tangential direction, the outlet opening is provided in the same direction as the oscillation, the liquid flows out of the vessel according to the oscillating speed of the vessel.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 is a partly cutaway front view of a first embodiment of a pump according to the present invention;

FIG. 2 is a sectional view taken on line II—II of FIG. 1;

FIG. 3 is a sectional view of a vessel portion of a pump according to a second embodiment;

FIG. 4 is a sectional view taken on line IV—IV of FIG. 3;

DETAILED DESCRIPTION OF THE PREFERRED EMBODIMENTS

Figure 5:
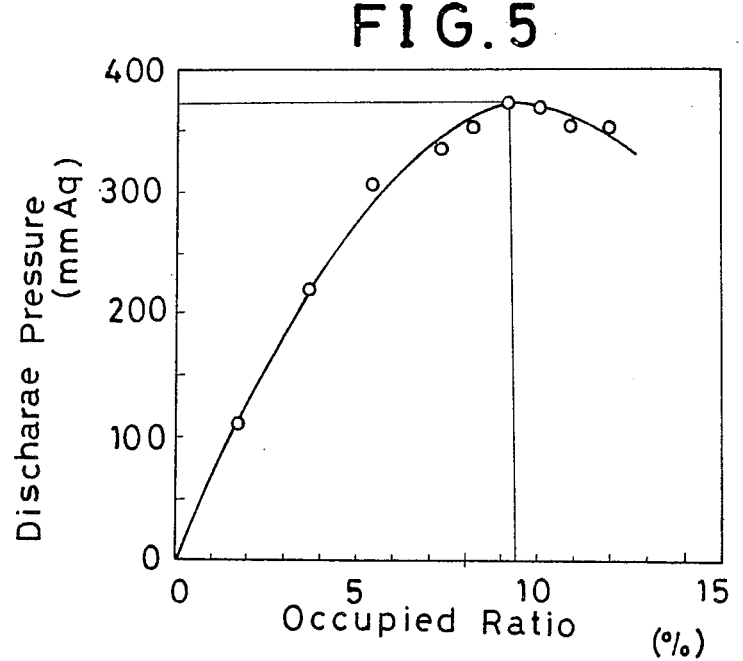
FIG. 5 is a graph showing the relationship between the occupied ratio of a float portion within the vessel and the discharge pressure, which means the pressure difference between inlet and outlet.

A first embodiment of a pump according to the present invention will be described hereinafter with reference to FIGS. 1 and 2.

A vessel indicated at 1, which is formed of synthetic resin or the like, has an inlet 2 in the vicinity of a center position at the upper part thereof and an outlet opening 3 extending in a tangential direction from an outer peripheral portion thereof, and is rotatably held by means such as a flexible pipe or a roller provided on the lower surface of the vessel, which will be described later. A projected recess 4 is provided in the lower surface of the vessel 1, and an electric motor 6 having a crank-like rotary shaft 5 loosely fitted into the recess 4 is provided at the lower part of the vessel 1. The rotational direction of the motor 6 is about an axis transverse to the tangential direction of the outlet opening 3. The end of the inlet 2 and the end of the outlet opening 3 are each connected to a flexible pipe or the like to permit free oscillation of the vessel 1.

With the above-described arrangement, the liquid flows in from the inlet 2 of the vessel and the motor 6 is energized to rotate the shaft 5. As a result of the eccentricity of the shaft, vessel 1 does not rotate but oscillates about shaft 5 in a plane transverse to the axis of rotation and containing the outlet opening 3, as indicated by the arrow in FIG. 2. Accordingly, the liquid within the vessel 1 gives rise to a circular motion to generate a centrifugal flow or eddy current in said direction indicated by the arrow and flows out of the outlet opening 3. The speed of the liquid flow is related to the speed of oscillation of the vessel 1 and can be adjusted by selection of the inside diameter of the outlet opening 3, the shape of a connecting portion of the outlet 3 with the vessel 1, and the like.

In order to use the pump in the above-described embodiment as a blood pump, contact of the blood with the exterior air should be avoided. This means that all the liquids need be sealed into the vessel 1. However, to function as a pump, it is necessary to let liquid within the vessel 1 move freely to mix the materials with different density in the liquid. Therefore, a vessel 1 in a second embodiment is an approximately cylindrical vessel with an inside diameter of 60 mm, a height of 40 mm and a capacity of 113 cm$^3$ and has a tangentially extending outlet 3 which curves upward at a point outside the vessel. As an experiment, a suitable number of synthetic-resin floats 7 having a diameter 10 mm were put into the vessel 1 to form a configuration corresponding to a different density material within the vessel 1, as shown in FIGS. 3 and 4. Several experiments were performed with such a construction by using blood as the liquid. When the vessel 1 was oscillated by rotation of shaft 5 in a direction as indicated by arrow A of FIG. 4, a group of floats 7 were rotated in synchronism therewith in a direction as indicated by arrow B to flow out with the liquid.

Next, the number of floats 7 accommodated within the vessel 1 was altered to change the occupied ratio of the different density material by the floats 7, and the discharge pressure of the pump was obtained by experiments, which is shown in the graph of FIG. 5. In this experiment, the number of revolutions of the vessel was 960 r.p.m. and the eccentric distance of the shaft 5 which is also the distance from the center of the revolution to the center of the vessel was 20 mm. As seen in FIG. 5, when the occupied ratio was 8 to 12%, the discharge pressure was approximately maximum.

Figure 6:
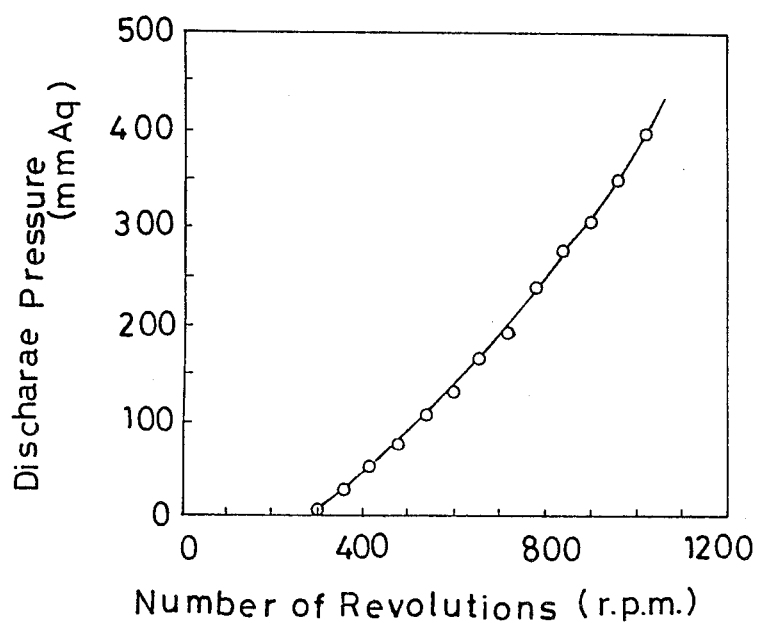
FIG. 6 is a graph showing the relationship between the number of revolutions of the vessel and the discharge pressure.
Figure 7:
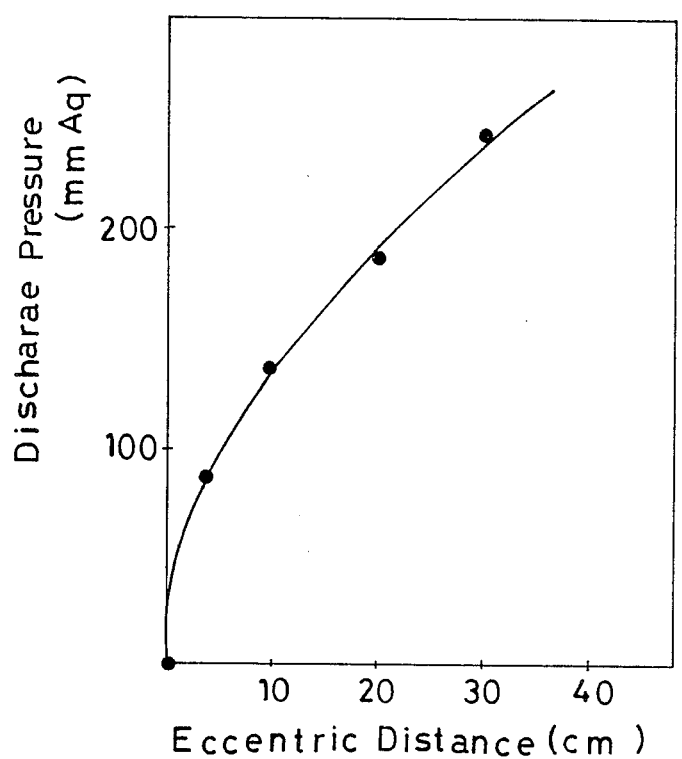
FIG. 7 is a graph showing the relationship between the eccentric distance from the center of revolution of the vessel and the discharge pressure.

Then, the aforesaid occupied ratio was set to 12% and the number of revolutions of the vessel was changed. The discharge pressure at that time was obtained by the experiment, which is shown in the graph of FIG. 6. As seen in FIG. 6, the discharge pressure increases in a relation of approximately the second power as the number of revolutions increases. Next, the eccentric distance was variously changed to obtain the discharge pressure by the experiment, whose results are shown in the graph of FIG. 7. In this experiment, the number of revolutions of the vessel was 960 r.p.m.

As seen in FIG. 7, the discharge pressure increases as the eccentric distance increases. The interrelation shown in the graphs of FIGS. 5 to 7 similarly applies to vessels which are different in size and shape.

Figure 8:
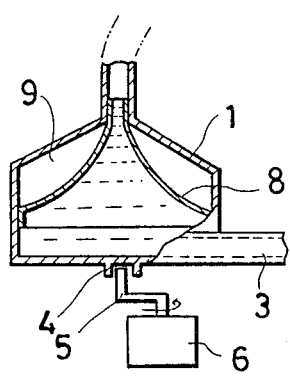
FIG. 8 is a partly cutaway view of a third embodiment.

FIG. 8 shows a third embodiment, in which a horn shaped membrane 8 formed of a flexible synthetic resin material comprising a soft film is secured at its upper and lower ends to the vessel 1, and air or other gas 9 is sealed in a space between the vessel 1 and the membrane 8. One can obtain a freedom for the volume of a centrifugal flow region of the liquid by use of the air space 9 and the resiliency of the membrane 8 in a centrifugal flow of liquid arising with the oscillation of the vessel, thus effectively producing a centrifugal flow to enhance the discharge performance. That is, optimum pumping performance can be achieved by setting the gas space at 8% to 12% of the vessel volume, in the same way as is achieved with the floats of FIG. 3.

Figure 9:
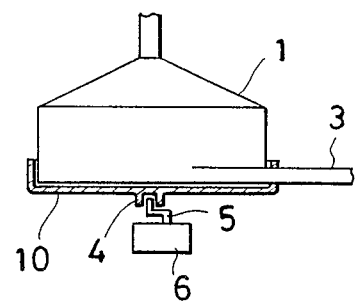
FIG. 9 is a partly cutaway view of a fourth embodiment.

FIG. 9 shows a fourth embodiment, in which the vessel 1 is supported by a tray-like support member 10 having at the lower surface thereof a recess 4 loosely fitted into the shaft 5. This can be conveniently applied to the case where the vessel 1 is formed of a material presenting problems in processing accuracy, mechanical strength or the like such as glass, synthetic resin or the like.

While in any of the aforementioned embodiments, the end of the shaft 5 is loosely fitted into the recess 4 in the lower surface of the vessel 1 or the support body 10, it is to be noted that a recess may instead be provided in the end of the shaft so that a projection projected from the lower surface of the vessel 1 or the support body 10 is loosely fitted into the recess of the shaft; in place of the recess and shaft or the loose fit of the projection, both the elements can be connected by rotatable connecting means such as a bearing.

Figure 10:
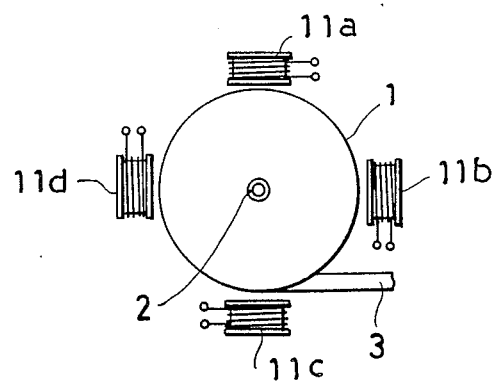
FIG. 10 is a plan view of a fifth embodiment.
Figure 11:
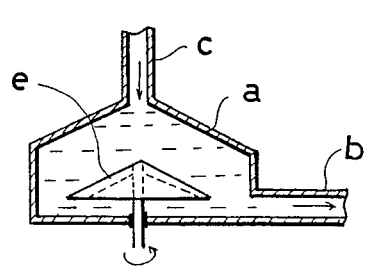
FIGS. 11 and 12 illustrate a conventional centrifugal pump.
Figure 12:
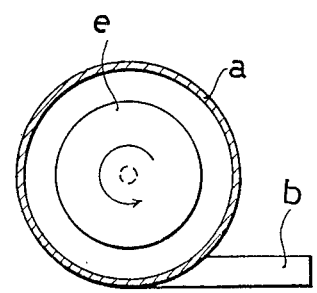

FIG. 10 shows a fifth embodiment, which shows another example of a driving device for oscillating the vessel 1, in which the vessel 1 is rotatably held by a means such as a roller positioned on the lower surface and is formed of an electromagnetic material such as permalloy.

Electromagnetic coils 11a, 11b, 11c and 11d are provided in opposition to the side of the vessel 1 at regular intervals, and when pulses from an oscillator are successively applied to the electromagnetic coils 11a, 11b, 11c, 11d, 11a, 11b . . . , the vessel 1 is oscillated due to the magnetic attraction between the electromagnetic material and the coils. In this embodiment, the connecting mechanism such as the recess 4 and the shaft 5 in the previously described embodiments is not provided, and therefore there occurs no mechanical wear, noises and the like, thus providing an excellent durability.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. An oscillating vessel pump comprising:
    a vessel having an inlet for liquid and an outlet opening in a tangential direction of an outer peripheral portion thereof;
    means for oscillating said vessel about an axis substantially transverse to said tangential direction; and
    a horned shaped membrane formed of a flexible synthetic resin, said membrane being positioned in said vessel and secured at upper and lower ends thereof to said vessel so as to form a gas space.

2. An oscillating vessel pump as defined in claim 1, wherein said inlet is formed in a central portion of an upper surface of said vessel.

* * * * *